US006506566B2

(12) United States Patent
Markvardsen et al.

(10) Patent No.: US 6,506,566 B2
(45) Date of Patent: *Jan. 14, 2003

(54) PHAGE DISPLAY FOR DETERGENT ENZYME ACTIVITY

(75) Inventors: Peter Markvardsen, Bagsvaerd (DK); Mads Eskelund Bjornvad, Frederiksberg (DK); Frank Mikkelsen, Valby (DK); Borge Diderichsen, Kobenhavn O (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/739,936

(22) Filed: Dec. 18, 2000

(65) Prior Publication Data

US 2002/0058246 A1 May 16, 2002

Related U.S. Application Data

(63) Continuation of application No. 09/017,612, filed on Feb. 2, 1998, now Pat. No. 6,194,183, which is a continuation of application No. PCT/DK96/00368, filed on Sep. 4, 1996.

(30) Foreign Application Priority Data

Sep. 7, 1995 (DK) .............................................. 0988/95

(51) Int. Cl.⁷ ...................... C12Q 1/68; G01N 33/573; G01N 33/53; C12N 9/99; C12N 7/02
(52) U.S. Cl. ........................ 435/6; 435/7.4; 435/7.6; 435/184; 435/239
(58) Field of Search ................................ 435/5, 6, 184, 435/7.4, 7.6, 239

(56) References Cited

U.S. PATENT DOCUMENTS

| | | | | |
|---|---|---|---|---|
| 4,663,071 A | * | 5/1987 | Bush et al. ............. | 252/174.19 |
| 5,096,815 A | | 3/1992 | Ladner et al. ............. | 435/69.1 |
| 5,223,409 A | | 6/1993 | Ladner et al. ............. | 435/69.7 |
| 5,837,517 A | * | 11/1998 | Sierkstra et al. ............. | 435/221 |
| 5,914,306 A | | 6/1999 | Svendsen et al. ............ | 510/392 |
| 6,190,900 B1 | * | 2/2001 | Sierkstra et al. ............. | 435/221 |
| 6,194,183 B1 | * | 2/2001 | Markvardsen et al. ...... | 435/183 |
| 6,303,340 B1 | * | 10/2001 | Pollitt et al. ................ | 435/69.7 |

FOREIGN PATENT DOCUMENTS

| | | | |
|---|---|---|---|
| DK | 0 396 608 B1 | * | 3/1996 |
| WO | WO 92/05249 | * | 2/1992 |
| WO | WO 93/17124 | | 9/1993 |
| WO | WO 95/22615 | | 8/1995 |

OTHER PUBLICATIONS

McCafferty J. et al, Phage–enzymes: expression and affinity chromatography of functional alkaline phosphates on the surface of bacteriophage, Protein Eng. 1991, 4/8, 955–961.*
Clackson T. et al, Making antibody fragments using phage display libraries, Nature, 1991, 352, 642–628.*
Fuchs P. et al, Targeting recombinant antibodies to the surface of Escherichia coli: fusion to the peptidoglycan associated lipoprotein, Biotechnology, 1991, 9, 1369–1372.*
Spee J. et al, Efficient random mutagenesis method with adjustable mutation frequency by use of PCR and dITP, Nucleic Acid Research, 1993, 21/3, 777–778.*
Hawkins R. E. et al, Selection of phage antibodies by binding affinity mimicking affinity maturation, J. Mol. Biol., 1992, 226, 889–896.*
Hoogenboom H. R. et al, Building antibodies from their genes, Immunologicall Reviews, 1992, 130, 41–68.*
Moore W. J. et al, Synthesis of peptides containing a sulfinamide or a sulfonamide transition–state isostere, Tetrahedron, 1993, 49, 1133–1150.*
Corey D. R. et al, Trypsin display on the surface of bacteriophage, Gene, 1993, 128, 129–134.*
Griffiths A. D. et al, Human anti–self antibodies with high specificity from phage display libraries, The EMBO Journal, 1993, 12, 725–734.*
Smith R. et al, An approach to Sequence–Specific antibody Proteases, Applied Biochemistry and Technology, 1994, 47, 329–343.*
Soumillion P. et al, Selection of beta–lactamase on filamentous bacteriophage by catalytic activity, J. Biol. Chem., 1994, 237, 415–422.*

(List continued on next page.)

Primary Examiner—Ponnathapu Achutamurthy
Assistant Examiner—Malgorzata A. Walicka
(74) Attorney, Agent, or Firm—Jason I. Garbell

(57) ABSTRACT

The invention relates to a method of identifying enzymes suitable for use in detergents, especially the selection of specific enzyme variants among a large number of such variants created through random mutagenesis. The method comprises that enzyme variants to be selected are in a mixture of enzyme variants which are each displayed on the surface of cells or phage particles, and (i) introducing the mixture into a detergent composition under conditions that will have a negative impact on the activity of or inactivate most of said enzyme variants, (ii) reacting said mixture with a catcher molecule that will bind specifically only to enzyme variants that exhibit the property sought for, (iii) separating said complex from the remaining parts of said mixture, (iv) dissociate said complex to isolate such cell(s) or phage(s) that displayed said enzyme variant without the catcher molecule, (v) introducing said phage into a host wherein it will multiply, or (va)cultivating said cell under conditions conducive to its multiplication, (vi) isolating a DNA molecule coding for said enzyme variant from the genome of said cell or phage, and (vii) determining the sequence of said DNA molecule. The invention further relates to specific materials used in said method, the enzymes selected by use of the method, and to detergent compositions comprising aid enzymes.

13 Claims, 1 Drawing Sheet

U.S. PATENT DOCUMENTS

Samuelson P. et al, Cell surface display of recombinant proteins on *Staphylococcus carnosus*, J. Bacteriology, 1995, 177, 1470–1476.*

Soumillion et al., Applied Biochemistry and Biotechnology, vol. 47, pp. 175–191 (1994).

Soumillion et al., J. Mol. Biol. vol. 237, pp. 415–422 (1994).

Kozlovska et al., Gene., vol. 137, pp. 133–137 (1993).

Crameri et al., Gene., vol. 137, pp. 69–75 (1993).

Bjerrum et al., Applied Gene Evolution, pp. 1–37.

Soumillion et al. (1994) Applied Biochem. and Biotech. 47, pp. 175–190.

* cited by examiner

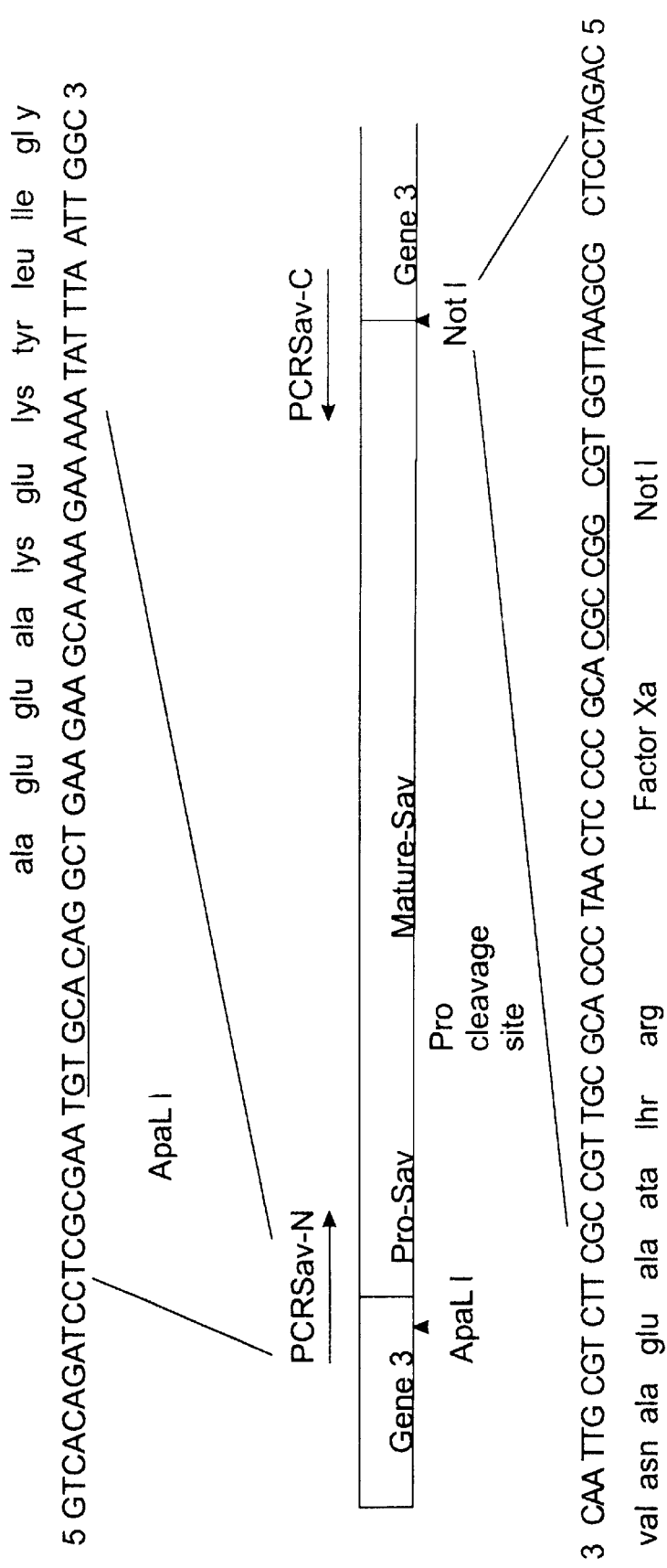

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 1:

GTCACAGATC CTCGCGAATG TGCACAGGCT GAAGAAGCAA AAGAAAAATA TTTAATTGG    60

(2) INFORMATION FOR SEQ ID NO: 2:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO: 2:

CAGATCCTCG CGAATTGGTG CGGCCGCACG CCCCTCAATC CCACGCGTTG CCGCTTCTG    60

GTTAAC    66

(2) INFORMATION FOR SEQ ID NO: 3:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO: 3:

GTCACAGATC CTCGCGAATG TGCACAGGAG GTCTCGCAGG ATCTGTTTAA CCAGTTC    57

(2) INFORMATION FOR SEQ ID NO: 4:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

CAGATCCTCG CGAATTGGTG CGGCCGCACG CCCCTCAATC CCAAGACATG TCCCAATTA    60

CCCGAAGTAC C    71

-continued (2) INFORMATION FOR SEQ ID NO: 5:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 5:

Ala Glu Glu Ala Lys Glu Lys Tyr Leu Ile Gly
1              5                   10

(2) INFORMATION FOR SEQ ID NO: 6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 6:

Val Asn Ala Glu Ala Ala Thr Arg
1              5

PHAGE DISPLAY FOR DETERGENT ENZYME ACTIVITY

CROSS-REFERENCE TO RELATED APPLICATIONS

This application is a continuation of U.S. Ser. No. 09/017,612 filed Feb. 2, 1998, now U.S. Pat. No. 6,194,183 which is a continuation of PCT/DK96/00368 filed Sep. 4, 1996 and claims priority under 35 U.S.C. 119 of Danish application serial no. 0988/95 filed Sep. 7, 1995, the contents of which are fully incorporated herein by reference.

FIELD OF THE INVENTION

The present invention relates to a method of identifying enzymes suitable for use in detergents, especially the selection of specific enzyme variants among a large number of such variants created through random mutagenesis.

The invention further relates to specific materials used in said method, the enzymes selected by use of the method, and to detergent compositions comprising aid enzymes.

BACKGROUND OF THE INVENTION

An increasing number of polypeptides, including enzymes and non-enzymatic proteins, are being produced industrially, for use in various industries, household, food/feed, cosmetics, medicine etc. The major source for these proteins is and have been microorganism found in nature. However, since science have developed many new techniques for creating variants of polypeptides through protein engineering, it is becoming increasingly important to be able to make huge populations of protein variants, to screen and select for new properties.

The classic approach for finding polypeptides with new and special properties, have been to screen wild type organism present in nature. This has been a very successful way of generating polypeptides to be used in such diverse areas as the above mentioned industries. Furthermore it is possible to generate new variants of a protein by classical mutation of the microorganism. However, since this approach is a very labour and time consuming process, researchers have in the last two decades been developing improvements on existing polypeptides by creating artificial diversity, using more specific and therefor faster techniques, such as protein and genetic engineering.

Such artificial diversity can be generated by using recombinant DNA techniques such as site-directed or random mutagenesis. This approach generates a population of polypeptide variants which can be selected according to the newly acquired phenotype of the given organism used for the experiments. Such phenotypic screen has its limitations according to the number of mutants it would be possible to screen. First of all one would have to set up a screening assay where a given new property of a polypeptide can be detected and the given mutant can be isolated. Then the DNA encoding the polypeptide is to be isolated and characterized.

These techniques have been used successfully to create new important polypeptides exhibiting improved properties, such as higher specific activity, higher stability under high or low pH, temperature stability, stability under oxidizing conditions etc.

However successful this approach has been, there is still a limitation in the number of polypeptides it is possible to screen and test by using these techniques. Therefore it is of interest to create novel systems, whereby it is possible to combine the screening and the selection in one procedure.

Furthermore such a procedure should make it possible to pick out only those variants with the best properties under given conditions, and these variants should be picked out of a variant population consisting of more than $10^8$ members.

One promising approach for making such artificial diversity and selecting for a new or improved specific polypeptide feature is the technique known as "phage display". This technique couples the genotype with the phenotype making it possible to select the two characteristics together. Hereby eliminating a couple of steps present in the above mentioned approaches.

Phage display is a fairly new technique first used and described by George P. Smith in 1988 (a first attempt was made in 1985). The earliest patents were granted to R. C. Ladner (U.S. Pat. Nos. 5,096,815 and 5,223,409) relating to "Generation and selection of novel DNA-binding proteins and polypeptides" and "Directed evolution of novel binding proteins", respectively. These two patents contain a wealth of references giving the background for the techniques.

Bacteriophage display systems have been developed that link a polypeptide or peptide of interest to the DNA that encodes it. Such display systems have been used to screen peptide libraries for binding to selected target molecules and to display functional proteins with the potential of screening these proteins for desired properties (see references 12 to 15).

Recently, improvements of the display approach have made it possible to express enzymes as well as antibody fragments on the bacteriophage surface thus allowing for selection of specific properties by selecting with specific ligands (see references 2–6, and 16–18).

For display of antibodies there is a large amount of references describing this successful approach. When it comes to the display of enzymes this is a less developed area, however there are some examples of this approach (see references 1, 8, and 10).

Especially the selection principles for enzyme phages are under evaluation and development. It has been shown that the enzymatic mechanism of a given enzyme can be used as means of binding principal by the use of suicidal inhibitors (see references 1 and 9).

SUMMARY OF THE INVENTION

The present invention relates to a method of selecting enzymes or enzyme variants suitable for use in detergents, wherein said enzyme variants to be selected are in a mixture of enzyme variants which are each displayed on the surface of cells or phage particles, comprising the following steps i) introducing said mixture into a detergent composition in fluid form under conditions that will have a negative impact on the activity of or inactivate most of said enzyme variants, ii) reacting said mixture with a catcher molecule that will bind specifically only to enzyme variants that exhibit the property sought for, to form a complex between said cell or phage displayed enzyme variant exhibiting the property sought for and said catcher, iii) separating said complex from the remaining parts of said mixture, iv) dissociate said complex to isolate such cell(s) or phage(s) that displayed said enzyme variant to be selected without the catcher molecule, v) introducing said phage into a host wherein it will multiply, or va) cultivating said cell under conditions conducive to its multiplication, and vi) isolating a DNA molecule coding for said enzyme variant from the genome of said cell or phage.

Another aspect of the invention relates to such enzymes that have been selected by use of the above method.

A further aspect of the invention relates to the use of detergents in the above method.

The invention also relates to a number of catcher molecules, such as suicide inhibitors and transition state analogs useful in the method of the first aspect of the invention.

Finally the invention relates to the enzymes produced by the method of the invention and detergent compositions comprising such enzymes.

BRIEF DESCRIPTION OF THE TABLES AND DRAWING

The invention is described in further detail below with reference to the Examples and Figures, wherein FIG. 1 shows the structure of the Savinase® gene 3 fusion, the sequence of the primers used for PCR of the Savinase® gene, and their relationship to the final structure with the cloning site underlined. For guidance, the amino acids encoded by the Savinase® and the sense strand of PCRSav-N are shown above the primers in lower case. (SEQ ID NO: 5) The PCRSav-C primer itself is drawn 3'–5'. (SEQ ID NO: 6)

DETAILED DESCRIPTION OF THE INVENTION

As indicated the present invention in its first aspect relates to a method of selecting enzymes or enzyme variants suitable for use in detergents, wherein said enzyme variants to be selected are in a mixture of enzyme variants which are each displayed on the surface of cells or phage particles, comprising the following steps i) introducing said mixture into a detergent composition in fluid form under conditions that will have a negative impact on the activity of or inactivate most of said enzyme variants, ii) reacting said mixture with a catcher molecule that will bind specifically only to enzyme variants that exhibit the property sought for, to form a complex between said cell or phage displayed enzyme variant exhibiting the property sought for and said catcher, iii) separating said complex from the remaining parts of said mixture, iv) dissociate said complex to isolate such cell(s) or phage(s) that displayed said enzyme variant to be selected without the catcher molecule, v) introducing said phage into a host wherein it will multiply, or va) cultivating said cell under conditions conducive to its multiplication, and vi) isolating a DNA molecule coding for said enzyme variant from the genome of said cell or phage.

Prior to performing the method of the invention it is necessary to express the enzymes to be investigated on the surface of a cell or phage.

This is conveniently done by first mutagenizing a DNA molecule coding for an enzyme of interest by random mutagenesis to create a large population or a library of mutated DNA molecules, each coding for an enzyme slightly different from the parent enzyme. The number of different DNA molecules generated thereby is extremely large, even up to more than $10^9$ mutants. Methods therefore are well known in the art, and reference is made to Spee et al. (21) describing such a method.

Each of the DNA fragments representing said library is inserted into a vector of a cell or phage in a site where said mutagenized DNA is adjacent to the DNA coding for a surface protein of said cell or phage, and in a manner by which said mutagenized DNA will be expressed and the corresponding enzyme variant displayed on the surface of the cell or phage when transferred into the cells of interest. This produces a DNA construct.

Examples of such surface proteins are the peptidoglycan associated lipoprotein of *E. coli* cell surface, protein A of *Staphylococcus aureus* or gIII protein of fd or M13 filamentous phages. These techniques are also well known and reference is made to references 2, 3, 11, and 22 for descriptions of such methods.

The transformed cells are then multiplied to generate a large population or library of cells or phages where each cell or phage displays one enzyme variant, and where each of these cells or phages carries DNA coding for the specific enzyme variant in its genome, thereby establishing a link between the phenotype and genotype of the cell or phage. The number of enzyme variants expressed are due to the degeneracy of the genetic code smaller than that of the DNA mutants, but still a very large number will be generated.

According to the invention this library is placed in a detergent under conditions which will inactivate most of said enzyme variants, and especially conditions which are known to be harmful for the activity of the parent enzyme, and/or where it is desired to select for enzyme variants exhibiting improved properties in respect of the parameter tested the conditions have a negative impact on the property being tested for.

As conditions that could inactivate or have a negative impact on the properties of the enzyme, the detergent could comprise oxidants (bleaching agents), various surface active agents, builders etc. to which it is desired to find enzyme variants that are (more) resistant against the influence of these agents, or the mixture could be treated at both high and low temperatures, or kept at pH values or ionic strengths, that would inactivate or exhibit a negative impact on the parent enzyme; or if the parent enzyme is a protease the mixture could be left for a prolonged time to select for enzymes resistant to autoproteolysis; or the detergent could comprise a protease in order to select for lipases, cellulases, amylases, etc. that are resistant to the proteolytic activity of said protease.

Other parameters that could be tested for comprises hydrophobic and hydrophilic interactions, solvation, and binding pockets for substrate, cofactors and allosteric factors. All parameters where subtle changes in the structure may provide for a change.

In other respects the detergents to be used in the method of the invention are of well known composition and reference is made to U.S. Pat. Nos. 4,663,071, 4,652,392, 4,507, 219, 4,405,483, 4,285,841, 4,284,532, 4,146,495, 4,144,226, 3,933,672, 3,929,678, 3,364,103, 3,308,067, 2,477,383, 2,220,099, 1,739,942, and German Patent Application DOS 2,124,526 for descriptions of such compositions and components thereof.

Thereafter the library is brought to react with a catcher molecule that will bind specifically only to displayed enzyme variants that have retained the properties sought for. Examples of such catcher molecules are suicide inhibitor for the enzymic activity of interest or transition state analogs.

In this context the expression "suicide inhibitor" means an irreversible inhibitor where the inhibitor is covalently bound to the enzyme after incubation. Active site directed irreversible inhibitors and mechanism based enzyme inhibitors are specific examples of this inhibitor type. References 1 and 9 describe such inhibitors.

In this context the expression "transition state analog" means a competitive inhibitor that structurally resembles the substrate portion of the unstable transition state of an enzymatic reaction. This type of inhibitor has a very high affinity for the enzyme. References 23 and 24 describe such analogs.

Since many of the enzyme variants being displayed by the cells or phages in the library now have been fully or partly inactivated, the catcher will only react with such displayed enzyme variants that still exhibit the property sought for and form a complex therewith.

The complexes must now be separated from the remaining cells or phages (those not displaying the property sought for, e.g. inactive enzyme variants) and other components of the detergent and reagents added together with the inhibitor.

Methods for this are well known in the art, e.g. from various immuno assay methods, and reference is made to references 1 and 7 for such methods.

One way of performing this separation is by binding the complex to a surface, such as the surface of a test tube, a well in a titer plate, or to particles.

In one type of embodiment the binding may be through adsorption or absorption to the surface.

In another embodiment the binding is through a covalent bond.

In this connection the inhibitor may be modified in various ways to be able to bind to the surface, or the surface is activated to bind the complex.

One specific manner is by treating the surface with streptavidin and biotinylating the catcher prior to reacting the catcher with the library.

If the complex has been bound to a surface said phage is released by using an agent that will dissociate the connecting entity or if adsorption has been used simply desorb the complexes, whereafter the catcher is removed by digestion or dissociation.

A convenient agent is a specific protease that will digest the enzyme variant displayed.

It is important that the agent used for this purpose does not harm the phage in question.

In a specific embodiment said digestion is performed with a protease, such as Factor IX.

Next the phage displaying the enzyme variant is amplified by infecting a host therewith. Said host is one wherein said phage multiplies in large numbers thereby providing an ample amount of DNA for sequencing.

In one embodiment of the invention said host is an *E. coli*, of the strain DH12S.

If the enzyme variant has been displayed on the surface of a cell, the cell is grown under conditions conducive for the proliferation thereof.

As the location of the enzyme variant DNA on the phage or cell genome is known it is then easy to isolate relevant DNA for the sequencing.

The information obtained from sequencing the DNA enable the skilled person to device other DNA constructs for introduction into suitable hosts for the actual production of the selected enzyme variants, which then can be used in detergents.

Suitable hosts will often be microorganisms, such as bacteria, yeast, or fungi of the same type or even strain that produced the parent enzyme. Such hosts, techniques for introducing DNA into them, and culturing and isolating the enzymes are all well known.

The method of the invention is designed for selecting enzyme variants for use in detergent formulations and the method will therefore often be used for the selection of variants of proteases, such as a subtilisins, preferably highly alkaline subtilisins, using catchers chosen from the group comprising suicide inhibitors and transition state analogs.

Another enzyme group of interest are the lipases, such as lipases from fungi such as Pseudomonas or Trichoderma etc., preferably Lipolase® and variants hereof, using catchers chosen from the group comprising suicide inhibitors and transition state analogs.

Further enzyme groups of interest are proteases (metallo, acid, neutral or alkaline), cellulases, amylases, lyases, xylanases, pectinases, polygalacturonases, oxidases, laccases, oxidoreductases, transglutaminases, galactosidases, phytases or peroxidases.

MATERIALS AND METHODS

*E. coli* strains:
 DH12S: Available from Life Technologies A/S, Roskilde, Denmark.
Vectors:
 fd-tet-DOG1: The construction of this vector is described in reference 16.
 pSX222: The construction of this plasmid is described in WO 91/00345 (NOVO NORDISK A/S). pSX222 contains a gene encoding the Savinase® protease.
 pSX222(M222A): pSX222 with a Savinase® mutant gene encoding the oxidation stable variant M222A (described in EP 396 608 B1).
 pSX581: The construction of this plasmid is described in WO 96/17943 (NOVO NORDISK A/S). pSX581 contains a gene encoding the Lipolase® lipase.
 pSX581(D96L): pSX581 with a mutated gene encoding the Lipolase® D96L Dobanol 25-7 stable variant (Described in WO 92/05249).
Restriction enzymes:
 If nothing else is mentioned all restriction enzymes are from New England Biolabs, Beverly, Mass., USA.
Catchers:
 A suicide inhibitor designated "suicide-Sav-1" is used. The inhibitor has the formula:

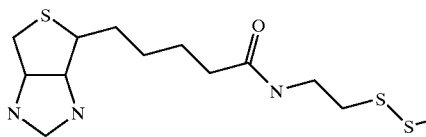
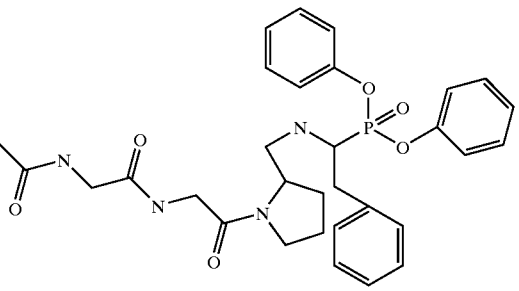

Another suicide inhibitor designated "suicide-Lip-1" is also used. The suicide-Lip-1 inhibitor is of the phosphonate irreversible inhibitor type (Björkling F. et al. "Inhibition of Lipases by phosphonates" Bioorganic & Medicinal Chemistry 2:697–705 (1994)), and has the formula:

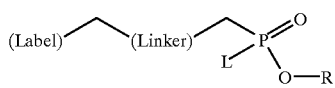

Wherein
L is a leaving group e.g. a halogen, such as Cl, or p-nitrophenyl, R is a straight or branched alkyl group with from 1 to 20 carbon atoms, such as ethyl, or a diglyceride like group. Label is a group or compound which can be used for recognition/identification and immobilisation selectively, such as biotin or digoxigenin, where Biotin is a hydrophilic and digoxigenin is a hydrophobic label.

Oligonucleotide synthesis:
All oligonucleotide primers were synthesized on an ABI 394 DNA/RNA synthesizer (Applied Biosystems, Foster City, Calif., USA).

DNA sequencing:
All DNA sequencing were done according to the ABI 2x Taq Protocol for the Taq Dye Deoxy™ Terminator Cycle Sequencing Kit. on an ABI Model 373A DNA Sequencer.

Characterization of the fd-Sav phases:
ELISA:
Binding of Enzyme phages was detected using standard ELISA techniques.

Briefly, wells of microtiter plates (Maxisorp, Nunc) were coated with 100 ml catcher solution (10 mg/ml in PBS of either streptavidin or polyclonal antibodies raised in rabbits towards Savinase® prepared at Novo Nordisk A/S) overnight at 4° C. followed by blocking with PBS containing 2% skimmed milk powder (Difco) for 2 hrs. at 37° C.

Serial dilutions in blocking solution of phages taken either directly from the phage preparation (for use in ELISA with polyclonal antibodies as catcher) or phages bound to biotinylated suicide inhibitor and washed as described above (for use in ELISA with streptavidin as the catcher) were added to the wells and incubated with rocking between one and two hrs at room temperature.

Washings between the different steps were done with PBS containing 0.05% Tween-20.

Binding was assayed using peroxidase-conjugated rabbit anti-M13 polyclonal antibodies (Pharmacia) followed by detection with ortho-phenylene-diamine (DAKO) according to the specifications by the manufacturer.

Detection reaction was left for 10–30 min before stopping by adding 50 ml of 2M $H_2SO_4$. Plates were read in a micro-titer plate reader set at $OD_{490}$.

Characterization of the fd-Lip phages:
The fd-Lip enzyme phages was characterised by demonstrating their lipase activity in the ELISA assay described immediately below.

ELISA microtiter plate assay:
Principle: A mixture of triglyceride and p-Nitrophenyl-fatty acid (pNP-FA) is coated to the walls of an ELISA plate-well. The method is based on the fact that the hydrolysis of esterbonds in the pNP-FA results in the release of p-Nitrophenol (yellow) into the supernatant and that the development of colour is followed on an ELISA-reader.

Apparatus: UV max. Kinetic microplate reader (Molecular Device)

Substrate solution:
0.5 mM Triolein (Sigma T-7140)
0.5 mM p-Nitrophenyl Palmitate (Sigma N-2752) in Hexan
0.5 mM olive oil
0.5 mM p-Nitrophenuyl caprylate in 96% Ethanol Buffer:
0.16 M Tris, pH 9

Procedure:
100 μl substrate mix is transferred to each well and the organic content is evaporated. 125 μl buffer and 75 μl fd-Lip phage enzymes (prepared as described in example 5) is added to the well. The microtiter plate is placed in the ELISA-reader and the development of colour is recorded.

In this ELISA lipase microtiter assay both fd-Lip and fd-Lip(D96L) enzyme phages showed lipase activity well above the background level of fd phages. This demonstrated the fd-Lip phages have lipase activity.

EXAMPLES

Example 1

Construction of fd-Sav and fd-SavM222A:
The Pro-Mature Savinase® gene was cloned into the Apa LI and NotI sites of the vector fd-tet-DOG1. The insert was prepared by polymerase chain reaction (PCR) using the primers shown in FIG. 1 and was derived from pSX222. The oligonucleotide primers were designed to generate a PCR product with an ApaLI restriction site at the 5' end of the gene and a NotI restriction site at its 3' end. The sequence of the oligonucleotide primers were:

PCRSav-N:
5'-GTC ACA GAT CCT CGC GAA TGT GCA CAG GCT GAA GAA GCA AAA GAA (SEQ. ID NO: 1)
AAA TAT TTA ATT GGC-3'

PCRSav-C:
5'-CAG ATC CTC GCG AAT TGG TGC GGC CGC ACG CCC CTC AAT CCC ACG (SEQ. ID NO: 2)
CGT TGC CGC TTC TGC GTT AAC-3'

The PCR was carried out in 100 ml of 10 mM Tris-HCL, pH 8.3 containing 250 mM each of dNTP, 50 mM KCl, 2.5 mM $MgCL_2$, 0.01% gelatine, 0.25 units/ml of Taq polymerase (Cetus/Perkin Elmer) and 0.5 ng/ml pSX222 template using a Perkin Elmer Cetus DNA Thermal cycler 480 with 30 cycles, consisting of 1 min at 92° C., 2 min at 50° C., and 3 min at 72° C. The construct so derived was called fd-Sav. The insert in fd-Sav was verified by sequencing.

The construction of fd-SavM222A was performed as for fd-Sav. Except that pSX222(M222A) was used as template in the immediately above described PCR reaction.

Example 2

Preparation of fd-Sav phage-enzyme:

*Escherichia coli* DH12S cells containing fd-Sav or fd-Sav (M222A) were grown for 16 h at 37° C. in 2 X TY with 15 mg ml tetracycline. Concentrated phage were prepared essentially as described in reference 10.

Briefly, Phage-enzyme cultures were clarified by centrifugation (15–20 min at 10.000 r.p.m., 8×50 ml rotor, Sorval RC-5B centrifuge). Phages were precipitated by adding ⅕ volume 20% polyethylene glycol, 2.5 M NaCl, left for 1 h at 4° C., and centrifuged (as above). Phage pellets were resuspended in 10 mM Tris-HCl, pH 8.0, to ¹⁄₁₀₀th of the original volume, and residual bacteria and aggregated phage removed by two centrifugation steps of 5–10 min each at 12000 r.p.m. in a microcentrifuge at 4° C.

Example 3

Selection of fd-SavM222A phages:

To establish reaction conditions, the PEG pellet of fd-Sav phage from 250 ml culture is resuspended in 1.5 ml of 50 mM acetate buffer at pH 5 to give about 1011 TU per ml, and filtered through a Millex-GV (0.22 mm). To 500 ml of this solution, 0.3 mg of inhibitor in 25 ml DMSO are added. Loss of Savinase activity is followed throughout the incubation by taking samples and measure the protease activity against the following substrate: Suc-ala-ala-pro-phe-pNA (SIGMA, St. Louis, Mo. USA).

After minimal conditions has been established for inhibition of the fd-Sav phage, several phages (fd-tet-DOG1, fd-SavM222A, fd-Sav) prepared as above are used to make predefined mixtures.

450 ml of phage mixture (1011 to 1012 TU per ml) is incubated for 30 minutes in a bleach containing detergent (Bleach containing detergents comprise oxidative chemicals. See EP 396.608 for more details). The phage mixture is added 50 ml of a solution of 10% (w/v) bovine serum albumin (BSA), then the biotinylated suicide inhibitor is added to (0.5) mM. The reaction is allowed to proceed for 30 minutes. The phages are precipitated by 200 ml of the PEG-NaCl solution and centrifugation. The pellet is resuspended in 500 ml of 50 mM acetate buffer at pH 5.0, and again PEG precipitated. The process is repeated, and the pellet is finally resuspended in 1.1 ml PBS buffer containing 2% (w/v) of non-fat dry milk powder (MPBS).

The actual binding selection using streptavidin as the catcher is carried out using either Immunotubes (Nunc, 3.5 ml volume) or microtiter-well plates (Nunc, 140 ml volume). Prior to selection the tubes or wells have been incubated with Streptavidin in PBS at a concentration of 100 mg/ml overnight at 4° C. and blocked for 2 h with PBS (Phosphate Buffered Saline 137 mM NaCl, 2.7 mM KCl, 4.3 mM $Na_2HPO_4 \times 7\ H_2O$, 1.4 mM $KH_2PO_4$ at pH 7.4) containing 2% Skimmed milk powder and 0.05% Tween-20 (Merck).

Binding of the phages bound to biotinylated inhibitor is carried out for 1–2 hours, followed by extensive washing (at least 10 times) with 10 volumes of PBS and 10 volumes of PBS containing 0.05% Twen-20.

For elution, the bound phages are resuspended in 1 ml 50 mM Tris:HCl, 100 mM NaCl, 1 mM $CaCl_2$ buffer at pH 8 (TNCB). The phages are eluted with gentle shaking at room temperature by incubation with 10 mg of factor Xa for 3 to 18 hours from Immunotube and microtiter well, respectively.

The eluted phages are used to infect the *E. coli* strain DH12S to prepare phages (50 ml of exponentially growing phages left for phage production overnight at 30–37° C.) for a further round of selection.

After a number of selection rounds it is possible to obtain a significant selection for the fd-SavM222A phage, which compared to the fd-Sav phage is oxidation stable (EP 396.608 B1). Preferably the selection ratio fdSavM222A/fd-Sav is higher than 8, more preferably higher than 10, and even more preferably higher than 20.

In general, higher numbers of selection rounds will normally give a more pronounced selection (higher selection number).

Example 4

Construction of fd-Lip and fd-Lip(D96L) phages:

The Mature Lipolase® gene was cloned into the Apa LI and NotI sites of the vector fd-tet-DOG1, essentially as described for fd-Sav (Example 1), except the PCR primers was now PCRLip-N and PCRLip-C (see below) and the PCR reaction was performed on pSX581 (for construction of fd-Lip) or pSX581(D96L) (for construction of fd-Lip (D96L).

```
PCRLip-N:
5'-GTC ACA GAT CCT CGC GAA TGT GCA CAG GAG GTC TCG CAG GAT CTG  (SEQ. ID NO: 3)
TTT AAC CAG TTC-3'

PCRLip-C:
5'-CAG ATC CTC GCG AAT TGG TGC GGC CGC ACG CCC CTC AAT CCC AAG  (SEQ. ID NO: 4)
ACA TGT CCC AAT TAA CCC GAA GTA CC-3'
```

Example 5

Preparation of fd-Lip phage-enzyme:

It was done as described for fd-Sav (Example 2), except the *Escherichia coli* DH12S cells now contained fd-Lip or fd-Lip(D96L).

Example 6

Selection of fd-LipD96L phages:

To establish reaction conditions, the PEG pellet of fd-Lip phage from 250 ml culture is resuspended in 1.5 ml of 50 mM acetate buffer at pH 5 to give about $10^{11}$ TU per ml, and fitered through a Millex-GV (0.22 mm). To 500 ml of this solution, Dobanol 25-7 is added in increasingly amounts (Dobanol 25-7 is a non-ionic surfactant). Loss of Lipase activity is followed throughout the incubation by taking samples and measure the protease activity against the following C-12 fatty acid Laurate substrate.

After minimal conditions has been established for inhibition of the fd-Lip phage, several phages (fd-tet-DOG1, fd-LipD96L, fd-Lip) is prepared as above and are used to make predefined mixtures.

450 ml of phage mixture ($10^{11}$ to $10^{12}$ TU per ml) is incubated for 30 minutes in a detergent containing the amount of Dobanol 25-7, just necessary to inactivate the fd-Lip phages (Se above). The phage mixture is added 50 ml of a solution of 10% (w/v) bovine serum albumin (BSA), then the biotinylated suicide inhibitor is added to (0.5) mM. The reaction is allowed to proceed for 30 minutes. The phages are precipitated by 200 ml of the PEG-NaCl solution and centrifugation. The pellet is resuspended in 500 ml of 50 mM acetate buffer at pH 5.0, and again PEG precipitated. The process is repeated, and the pellet is finally resuspended in 1.1 ml PBS buffer containing 2% (w/v) of non-fat dry milk powder (MPBS).

The actual binding selection using streptavidin as the catcher is carried out using either Immunotubes (Nunc, 3.5 ml volume) or microtiter-well plates (Nunc, 140 ml volume). Prior to selection the tubes or wells have been incubated with Streptavidin in PBS at a concentration of 100 mg/ml overnight at 4° C. and blocked for 2 h with PBS (Phosphate Buffered Saline 137 mM NaCl, 2.7 mM KCl, 4.3 mM $Na_2HPO_4 \times 7 H_2O$, 1.4 mM $KH_2PO_4$ at pH 7.4) containing 2% Skimmed milk powder and 0.05% Tween-20 (Merck).

Binding of the phages bound to biotinylated inhibitor is carried out for 1–2 hours, followed by extensive washing (at least 10 times) with 10 volumes of PBS and 10 volumes of PBS containing 0.05% Twen-20.

For elution, the bound phages are resuspended in 1 ml 50 mM Tris:HCl, 100 mM NaCl, 1 mM $CaCl_2$ buffer at pH 8 (TNCB). The phages are eluted with gentle shaking at room temperature by incubation with 10 mg of factor Xa for 3 to 18 hours from Immunotube and microtiter well, respectively.

The eluted phages are used to infect the *E coli* strain DH12S to prepare phages (50 ml of exponentially growing phages left for phage production overnight at 30–37° C.) for a further round of selection.

After a number of selections rounds it is possible to obtain significant selection for the, compared to fd-lip, Dobanol 25-7 stable fd-LipD96L phage (WO 92/05249). Preferably the selection ratio fdLipD96L/fd-Lip is higher than 8, more preferably higher than 10, and even more preferably higher than 20.

In general, higher numbers of selection rounds will normally give a more pronounced selection (higher selection number).

REFERENCES CITED IN THE SPECIFICATION

1. Soumillion, P., Jespers, L., Bouchet, M., Marchandbrynaert, J., Winter, G. and Fastrez, J. (1994) *Journal Of Molecular Biology*, 237, 415–422.

2. Hoogenboom, H. R., Marks, J. D. and Winter, G. (1992) *Immunological Reviews*, 130, 41–68.

3. Griffiths, A. D., Malmqvist, M., Marks, J. D., Bye, J. M., Embleton, M. J., Mccafferty, J., Baier, M., Holliger, K. P., Gorick, B. D., Hughesjones, N. C. and Winter, G. (1993) *Embo Journal*, 12, 725–734.

4. Orum, H., Andersen, P. S., Oster, A., Johansen, L. K., Riise, E., Bjørnvad, M. and Engberg, J. (1993) *Nucleic Acids Research*, 21, 4491–4498.

5. Barbas, C. F., Amberg, W., Simoncsits, A. and Lerner, R. A. (1993) *Gene*, 137, 57–62.

6. Hoogenboom, H. R. and Winter, G. (1992) *Journal Of Molecular Biology*, 227, 381–388.

7. Hawkins, R. E., Russell, S. J. and Winter, G. (1992) *Journal Of Molecular Biology*, 226, 889–896.

8. Corey, D. R., Shiau, A. K., Yang, Q., Janowski, B. A. and Craik, C. S. (1993) *Gene*, 128, 129–134.

9. Soumillion, P., Jespers, L., Bouchet, M., Marchandbrynaert, J., Sartiaux, P. and Fastrez, J. (1994) *Applied Biochemistry And Biotechnology*, 47, 175–190.

10. Mccafferty, J., Jackson, R. H. and Chiswell, D. J. (1991) *Protein Engineering*, 8, no 4, 955–961.

11. Samuelson, P., Hansson, M., Ahlborg, N., Andreoni, C., Gotz, F., Bachi, T., Nguyen, T. N., Binz, H., Uhlen, M. and Stahl, S. (1995) *Journal Of Bacteriology*, 177, 1470–1476.

12. Smith, G. P. (1985) *Science*, 228, 1315–1317.

13. Parmley, S. F. and Smith, G. P. (1988) *Gene*, 73, 305–318.

14. Scott, J. K. and Smith, G. P. (1990) *Science*, 249, 386–390.

15. Devlin, J. J., Panganiban, L. C. and Devlin, P. E. (1990) *Science*, 249, 404–406.

16. Clackson, T., Hoogenboom, H. R., Griffiths, A. D. and Winter, G. (1991) *Nature*, 352, 624–628.

17. Kang, A. K., Barbas, C. F., Janda, K. D., Benkovic, S. J. and Lerner, R. A. (1991) *Proceedings Of The National Academy Of Sciences Of The United States Of America*, 88, 4363–4366.

18. Breitling, F., Dübel, S., Seehaus, T., Klewinghaus, I. and Little, M. (1991) *Gene*, 104, 147–153.

19. Bryan, P. N., Rollence, M. L., Pantoliano, M. W., Wood, J., Finzel, B. C., Gilliland, G. L., Howard, A. J. and Poulos, T. L. (1986) *Protein Struct. Funct. Genet.*, 1, 326–334.

20. Strausberg, S. L., Alexander, P. A., Gallagher, D. T., Gilliland, G. L., Barnett, B. L. and Bryan, P. N. (1995) *Bio-Technology*, 13, 669–673.

21. Spee, J. H., Willem, M. and Kuipers, O. P. (1993) *Nucleic Acids Research*, 21, 777–778.

22. Fuchs, P., Breitling, F., Dübel, S., Seehaus, T. and Little, M. (1991) *Bio-Technology*, 9, 1369–1372.

23. Smith, R. M., Yuan, P., Weiner, D. P., Dutton, C. R. and Hansen, D. E. (1994) *Applied Biochemistry And Biotechnology*, 47, 329–343.

24. Moree, W. J., Vangent, L. C., Vandermarel, G. A. and Liskamp, R. M. J. (1993) *Tetrahedron*, 49,1133–1150.

What is claimed:

1. A method for selecting an enzyme for use in detergents, said method comprising:
   (i) providing a library of phages transformed with DNA encoding a plurality of variants of a parent enzyme and a control library of phages transformed with DNA encoding said parent enzyme, wherein said variants and said parent enzyme are displayed on the surface of said phages in enzymatically active form;
   (ii) contacting said control phage library with a detergent composition to form a mixture under selective conditions that have a negative impact on the enzymatic activity of said parent enzyme; wherein said selective conditions are selected from the group consisting of high temperature, low temperature, oxidative conditions, proteolytic conditions, pH conditions, ionic conditions, a surface active agent that has a negative impact on the enzymatic activity of the parent enzyme, a builder that has a negative impact on the enzymatic activity of the parent enzyme, a cofactor that has a negative impact on the enzymatic activity of the parent enzyme and combinations of any of the foregoing;
   (iii) physically separating (a) phages that display variant enzymes whose enzymatic activity is maintained under said selective conditions from (b) phages that display variant enzymes whose enzymatic activity has been negatively impacted under said selective conditions, to obtain a population of phages enriched for variant enzymes whose enzymatic activity is maintained under said selective conditions;
   (iv) isolating and amplifying DNA derived from individual phages of (iii)(a); and
   (v) determining the sequence of the variants encoded by the DNA isolated in step (iv).

2. A method as defined in claim 1, further comprising propagating the enriched phage population obtained in step (iii) and repeating steps (ii) and (iii).

3. A method as defined in claim 1, wherein said enriched phage population obtained in step (iii) contains at least about 8 times as many phages that display variant enzymes as phages that display the parent enzyme.

4. A method as defined in claim 1, wherein step (iii) comprises:
   1) contacting said mixture with a catcher molecule that binds selectively to enzymatically active enzymes, under conditions in which a complex is formed between the catcher molecule and the phages of (iii)(a) and complexes are not formed between the catcher molecule and the phages of (iii)(b);
   2) binding said complexes to a solid support;
   3) removing the bulk phage population; and
   4) recovering the bound phage.

5. A method as defined in claim 4, wherein said binding step comprises adsorption of said complexes to said solid support.

6. A method as defined in claim 4, wherein said binding step comprises covalent binding of said complexes to said solid support.

7. A method as defined in claim 5, wherein said catcher molecule is biotinylated and said solid support comprises streptavidin.

8. A method as defined in claim 4, wherein said recovering step is achieved using proteolysis.

9. A method as defined in claim 1, wherein step (iv) comprises:
   a) introducing said physically separated variant phages into a host to produce a transformed host library;
   b) isolating clones of individual transformed cells; and
   c) cultivating the host library under conditions that allow amplification of said variant-encoding DNA.

10. A method as defined in claim 1 wherein said parent enzyme is selected from the group consisting of a protease, a lipase, an oxidoreductase, an amylase, a lyase, a cellulase, a xylanase, a pectinase, a polygalacturonase, a transglutaminase, and a galactosidase.

11. A method as defined in claim 10, wherein said protease is a subtilisin.

12. A method as defined in claim 4, wherein said catcher molecule is selected from the group consisting of suicide inhibitors and transition state analogs.

13. A method as defined in claim 4, wherein said binding step comprises absorption of said complexes to said solid support.

* * * * *